United States Patent [19]
Gustafsson et al.

[11] Patent Number: 6,007,529
[45] Date of Patent: Dec. 28, 1999

[54] CONTAINERS FOR PARENTERAL FLUIDS

[75] Inventors: Bo Gustafsson, Alunda; Stefan Lundmark, Höganäs; Kjell Berglund, Järfälla; Cathrine Brooling, Bromma; Otto Skolling, Solna, all of Sweden

[73] Assignee: Pharmacia & Upjohn AB, Stockholm, Sweden

[21] Appl. No.: 08/905,547

[22] Filed: Aug. 4, 1997

Related U.S. Application Data

[60] Provisional application No. 60/023,194, Aug. 5, 1996.

[30] Foreign Application Priority Data

Apr. 10, 1996 [SE] Sweden .................................. 9601348

[51] Int. Cl.⁶ .............................. A61M 1/00; B65D 81/32
[52] U.S. Cl. .......................... 604/410; 604/416; 206/219
[58] Field of Search ..................................... 604/408, 410, 604/411, 415, 416, 82, 85, 87; 206/219, 221; 383/38, 210, 211

[56] References Cited

U.S. PATENT DOCUMENTS

| | | | |
|---|---|---|---|
| 4,507,114 | 3/1985 | Bohman et al. | 604/87 |
| 4,558,605 | 12/1985 | Iwamoto et al. | 604/410 |
| 4,872,553 | 10/1989 | Suzuki et al. | |
| 4,997,083 | 3/1991 | Loretti et al. | |
| 4,998,400 | 3/1991 | Suzuki et al. | |
| 5,114,004 | 5/1992 | Isono et al. | 206/222 |
| 5,128,414 | 7/1992 | Hwo. | |
| 5,176,634 | 1/1993 | Smith et al. | |
| 5,209,347 | 5/1993 | Fabisiewicz et al. | 206/219 |
| 5,267,646 | 12/1993 | Inoue et al. | 206/204 |
| 5,378,428 | 1/1995 | Inoue et al. | |
| 5,423,421 | 6/1995 | Inoue et al. | 206/219 |
| 5,458,244 | 10/1995 | Emori | 206/219 |
| 5,462,526 | 10/1995 | Barney et al. | 605/85 |
| 5,501,887 | 3/1996 | Tanaka et al. | 206/219 |
| 5,706,937 | 1/1998 | Futgawa et al. | 206/221 |

FOREIGN PATENT DOCUMENTS

| | | |
|---|---|---|
| 0345774B1 | 6/1989 | European Pat. Off. |
| 0444900B1 | 2/1991 | European Pat. Off. |
| 0460796A2 | 4/1991 | European Pat. Off. |
| 0510687A2 | 4/1992 | European Pat. Off. |
| 0639364A1 | 4/1993 | European Pat. Off. |
| 4233817C1 | 10/1992 | Germany. |
| 08100089A | 9/1994 | Japan. |
| 2134 067A | 12/1983 | United Kingdom. |
| WO94/19186 | 9/1994 | WIPO. |
| WO95/26177 | 10/1995 | WIPO. |
| WO95/33651 | 12/1995 | WIPO. |

OTHER PUBLICATIONS

Gauthier, William J., et al., "Elastomeric Poly(propylene): Influence of Catalyst Structure and Polymerization Conditions on Polymer Structure and Properties," American Chemical Society, Macromolecules, vol. 28, No. 11, 1995.

*Primary Examiner*—Ronald Stright
*Assistant Examiner*—David J. Cho
*Attorney, Agent, or Firm*—Gilberto M. Villacorta; Pepper Hamilton LLP

[57] ABSTRACT

A flexible transparent container for improved storage of oxygen sensitive parenterally administerable agents comprising an inner, primary container enclosed in a substantially oxygen impermeable outer envelope with an oxygen absorber, capable of consuming essentially all residual oxygen after the outer envelope is sealed, and for sufficient period also the oxygen penetrating said envelope. The inner container is made of a polypropylene containing flexible polymeric material compatible with lipophilic agents capable of forming both permanent and peelable seals, while the envelope is made of a substantially water impermeable flexible multilayered polymeric material comprising a first outer substantially water impermeable polymeric film with oxygen barrier forming capacity, assembled with a second, inner polymeric film with a supplementary oxygen barrier forming capacity. The container essentially maintains its characteristics after being subjected to sterilization by steam or radiation.

32 Claims, 2 Drawing Sheets

CONTAINERS FOR PARENTERAL FLUIDS

This case claims benefit of Provisional Application Ser. No. 60/023,194 filed Aug. 5, 1996.

FIELD OF INVENTION

The present invention relates to flexible polymeric containers with an improved long term storage capacity of such sensitive medical fluids that are intended to be administered parenterally. The containers have ability to withstand several types of final sterilization after being filled with medical fluids and seals, substantially without losing its barrier capacity or any other important characteristics. It comprises an outer sealed airtight envelope and an inner container filled with one or several medical agents which has high compatibility also to stored lipophilic agents.

BACKGROUND OF THE INVENTION

Traditionally, fluids aimed for parenteral administration to the blood stream of patients have been packaged in glass containers. There has, however, been much industrial efforts devoted to find alternative polymeric materials which are less resource consuming, cheaper and more convenient to handle than glass.

As discussed in, for example the International patent application WO 94/19186 (in the name of Pharmacia AB and Wipak Vihury Oy), it is considerable amount of technical problems that must be solved before a polymeric material with satisfying properties for storing parenterally injectible fluids is obtained. The material and container made thereof should be capable of withstanding different sterilization techniques without losing important characteristics, such as forming both an oxygen barrier and moisture barrier against the environment. They shall be compatible with fluids to be stored, even after a long term storage and even if the fluids contain lipophilic constituents that might lead to migration and dissolution of unwanted compounds from the polymeric matrix. In addition, the materials must be possible to weld together and be printable and maintain their flexibility and other mechanical properties, as well as their aesthetic appearance (i.e. transparency) after the sterilization procedure. It is also an important requirement that such a container shall be sterilized as a final step, after being filled and assembled, to provide the highest possible safety for the patients. It has been found that not even the highly sophisticated multilayer films according to the mentioned WO 94/19186 will be completely capable of meeting the highly rigorous requirements of keeping an oxygen barrier, when it is desired to store such sensitive fluids as lipid emulsions containing polyunsaturated fatty acids, for such a long time as several months in room temperature after autoclavation in a single package.

However, so far it has not been regarded as possible to obtain all the desirable properties combined in a single material and arrive with a cheap, convenient construction which also is environment friendly and possible to recycle by its manufacturer. For example, in the U.S. Pat. No. 5,176,634 to McGaw Inc., it is disclosed a flexible container having three chambers separated by frangible seals, in which diluents and medicaments are separately stored until the seals are ruptured to mix the contents together for delivery to a patient. If it is necessary to form a sheltering barrier against environmental oxygen for a stored product, this patent suggests the introduction of an aluminum foil as a complement to the multilayered polymeric material of the container. Such a mixture of metal and polymers in the same package, would however not, be desirable from an environmental viewpoint, since a recollection and recycling of the material would be difficult. Furthermore, the U.S. Pat. No. 5,176,634 does not particularly teach containers that can be steam sterilized after their assembly and filling which is a precondition for container systems for long term storage of parenteral nutrients intended to substitute glass bottles. The container disclosed in U.S. Pat. No. 5,176,634 obviously will be less suitable for separate storage of two or more steam sterilized parenteral nutrients.

The U.S. Pat. No. 4,997,083 in the name of Vifor S.A. discloses a flexible three-chamber bag for separate storage of lipids, amino acid and sugar to be mixed within the bag and used parenterally. For the mixing of the ingredients, transfer passages between the chambers are opened from the outside by the user. It is a drawback with this type of containers that the mixing will be relatively slow and complicated, especially if all the chambers are filled to a high degree and liquid must be pushed back and forth through the passages in order to complete the mixing procedure. If the lower mixing chamber is made large enough to comprise the volume of all three constituents during the mixing, the lower chamber must be filled with a large head space which gives disadvantages during the sterilization and storage of the products and leads to a poor utilization of the polymeric packaging material. Furthermore, the polymerized materials suggested to constitute the flexible bag in the U.S. Pat. No. 4,997,083 will not be sufficient to keep the nutrients from oxidative degradation after long term storage.

The International patent application WO 95/26117 in the name of Fresenius AG discloses a more convenient type of multi-chamber bag wherein the partition between the chambers are made by a weak welding possible to rupture to immediately obtain a large mixing cross-sectional area without the risk of tearing away parts of the breakable means. Even if this bag is made of a specifically designed multilayer foil having a sealant layer capable of forming different type of weldings at different temperatures, it will not be able to form a satisfactory oxygen barrier to protect highly sensitive contents during long time storage after autoclavation. Also its construction having filling tubes in the permanent seams sealing the chambers constitutes a risk of leakages and may cause problems if it is desired to have an additional airtight enclosure. This container therefore seems less suitable as a three-chamber container for joint separate storage of lipid emulsion, carbohydrates and amino acid solutions. Moreover, the exemplified incorporation of a paraffin oil in the multilayered material, would hardly be compatible with the storage of lipid emulsion when considering the risk for migration.

Also the British patent specification GB 2 134 067, in the name C.R. Bard Inc., discloses a flexible three compartment package having rupturable seals between the chambers to enable mixing before dispensing of its contents. This package will, however not, for material reasons be suitable for parenteral medical products, such as infusible nutrients.

The U.S. Pat. No. 4,872,553 in the name of Material Technology Engineering teaches a single chamber container made of polymers, suitable for storing an amino acid solution aimed for parenteral nutrition, while the U.S. Pat. No. 4,998,400, assigned to the same company, discloses a method of making such a container. It is disclosed how to fill and seal an inner primary container in an inert atmosphere, whereupon it is enclosed in an outer envelope together with a deoxidizer and autoclaved. The inner container consists of a linear low density polyethylene while the outer envelope consists of a three-layered laminated film formed of an outer nylon layer, a middle layer of an ethylene-vinyl alcohol copolymer and an inner polypropylene layer. Such a material will, however, not be possible to steam sterilize with maintained quality at 121° C. as required by the European Pharmacopoeia. However, not even such a container is likely to be entirely successful to provide a barrier for atmospheric oxygen after autoclavation and during long-term storage, up to 12 months or more, of more sensitive fluids, like lipid emulsions based on triglyceridic oils rich in polyunsaturated fatty acids and certain amino acids. The teachings of U.S. Pat. No. 4,998,400 indicates that the outer envelope risks to lose important characteristics by the steam sterilization. In one embodiment it is suggested that only the inner container shall be autoclaved. The inner container is thereafter cooled in an inert atmosphere and finally enclosed with the oxygen impermeable envelope. Such a process is not completely satisfying since it for rational reasons is desirable to make the sterilization step on the finally filled and assembled container. In another embodiment it is suggested that the finally assembled and sealed container is autoclaved. However, in order to retain the oxygen barrier after the autoclavation an extra drying process must be introduced in order to remove absorbed moisture from outer envelope.

The European Patent Application EP 0 639 364 by Otsuka Pharm. Factory Inc. discloses another recent flexible multi-chamber bag for storage of oxygen sensitive agents. This bag is preferably useful for storing degradable powder formed drug and its diluent in separate chambers. The chamber filled with the oxygen sensitive powder is covered with an oxygen barrier forming envelope which is sealed in a controlled atmosphere by weldings to the bag. A drawback with the containers exemplified in this application is that they may not withstand autoclavation after their final assembly.

It is obvious that the construction of a flexible multi-chamber container intended to substitute glass bottles for storing parenteral nutrients, such as lipid emulsions is a highly complex development process. A careful consideration must be taken to the capacity of the materials of being autoclavable with maintained characteristics, to their capacity of providing a barrier against environmental oxygen and water vapor, while at the same time it must be easy to process to a functional multi-chamber container, for example with conventional welding technology and comply with the demands of being possible to recollect and recycle in one single, simple process. For the parts of the container in contact with the stored, often lipophilic substances, it is a requirement that potentially hazardous agents must not be allowed to migrate into the parenteral product. Conventionally employed polymers in medical packages, like polyvinyl chlorides (PVC), and other polymers containing migrating plasticizers therefore can not be considered. Nevertheless, these polymeric materials have a higher permeability to oxygen than glass bottles which makes them unsuitable for long-term storage of especially sensitive fluids. Moreover, the material must have an aesthetically attractive appearance with a transparency that do not deteriorate after sterilization and storage. In addition, the material must allow printing of instructions and filling levels without migration of the printing ink. It is also important that the material maintains all the mechanical characteristics, such as flexibility and strength, after the sterilization independently, if it is performed by steam or radiation. Besides the important material properties, the container must be convenient to handle when mixing the stored products and provide a high degree of safety for the patient, both when considering the manufacture of the container and its handling by the user either in the home of a patient or at a hospital.

It is an object of the present invention to provide a flexible container of substantially made of a polymeric material with an improved barrier against environmental oxygen and moisture which also is capable of withstanding sterilization by means of high pressure steam (autoclavation) or irradiation essentially without losing any such barrier capacity or other important characteristics including flexibility or transparency, so even stored agents of high oxygen susceptibility may be stored for long periods with maintained integrity.

It is also an object of the present invention to provide a flexible container for separated long term storage of such agents that are easily perishable when stored together in their final parenterally administerable form and provide the container with means for mixing such agents aseptically within the container to an injectible fluid.

It is a particular object of the present invention to provide such a container for storing parenteral nutrition components separately, i.e. a lipid emulsion, a carbohydrate solution and an amino acid solution, and subsequently, just before parenteral administration, combine them to a homogenous fluid nutrient mixture.

It is another particular object of the present invention to prolong the possible storage period both in a cold environment and in room temperature for sensitive fluids aimed for total parenteral nutrition to overcome the problem of short shelf-life of such products.

It is still another object of the invention to provide a container with the capacity of separately storing several components filled in ready-made inner container which has a minimized number of potential sites where leakages can appear.

It is a further object of the present invention to provide such containers which are safe and convenient to handle and which minimize the risks for erroneous handling and contamination during all the steps necessary to obtain a parenterally administerable fluid of a predetermined quality.

It is a still further object of the present invention to provide such containers that are cheap and environment friendly by being to a high extent made of such polymeric materials which are possible to recollect and recycle together without an inconvenient dismembering of different container parts.

It is also an object of the present invention to provide a process for manufacturing such filled containers that are sterilized as a last stage after being assembled and filled, wherein the filling process is performed in a manner that avoids permanent, potentially leaking filling ports.

These objects of the present invention, as well as other obvious advantages demonstrated in this text, are attained by the appended claims.

DESCRIPTION OF THE INVENTION

The container according to the present invention is aimed for improved storage of oxygen sensitive parenterally administerable agents and consists generally of an inner, primary container enclosed in a substantially oxygen impermeable outer envelope with an oxygen absorber which is capable of consuming essentially all residual oxygen after the outer envelope is sealed, and for sufficient period also the oxygen penetrating said envelope. Both the inner container and the enclosing outer envelope are made of flexible and transparent polymeric materials. The inner container is made of a polypropylene containing flexible polymeric material compatible with lipophilic agents capable of forming both permanent and peelable seals and the envelope is made of a substantially water impermeable flexible multilayered polymeric material comprising a first outer substantially water impermeable polymeric film with oxygen barrier forming capacity, assembled with a second, inner polymeric film with a supplementary oxygen barrier forming capacity.

An important feature of the assembled container is that is essentially maintains its characteristics of forming an oxygen and moisture vapor as well as transparency and flexibility after being subjected to sterilization by steam or radiation. The inner container can be a single or multi-chamber container filled with one or several parenterally administerable agents. According to a particular important embodiment of the present invention, the inner primary container is divided into two or more chambers by one or more leaktight seals which are possible to rupture by hand from the outside of the container when the contents of the chambers are desired to be mixed to a homogenous fluid and administered to a patient by infusion or injection. For this reason, the inner container is provided with a fluid communication port in its bottom through which the mixed product can be received and through which additional agents can be supplemented to either to the mixed product or to the agent stored in the lower chamber. The port is attachable to conventional infusion devices and other devices useful for parenteral administration and will preferably have separate orifice for introduction and collection of fluid agents. Both the inner container and the sealing envelope are made of specifically selected polymeric materials which will be described in more detail below. As also will be explained in more detail below, the envelope is finally sealed in a protected atmosphere and in the space between said envelope and the inner container an oxygen scavenger is placed.

The agents stored in the containers according to the invention are preferably oxygen sensitive fluids or powders which otherwise lose activity or suffer from degradation during extended storage. Example of such agents are parenteral nutrients such as lipid emulsions containing oxygen sensitive polyunstaurated fatty acids, amino acids containing sensitive amino acids like cystein and many pharmaceutical agents which lose activity when stored in dissolved or diluted form and consequently must stored as a solid powder (lyophilized) form or as a concentrate separated from a diluent. Another example of agents that will benefit from storage in the inventive containers are such that must be kept separate during sterilization by means of heat like solutions of carbohydrates and solutions of amino acids which together may form discoloring complexes.

The inventive multi-chamber containers are manufactured according to a general method, wherein a bag shaped sealed inner container is formed from a flexible polymeric material by welding together its polypropylene containing sealing layers. At least two leak tight chambers are formed by welding at least one peelable seal seam possible to rupture by hand from the outside of the container. One side of the container is provided with temporary openings to the chambers which are filled with the parenterally administerable fluids, whereupon the temporary openings are sealed again by welding permanent seams. The filled and sealed inner container is enclosed in an oxygen barrier forming envelope together with an oxygen absorber which is sealed by welding in a controlled atmosphere. The so finally assembled is sterilized by means of steam or by irradiation.

The following detailed description aims to describe preferred embodiments and specific examples of containers and methods of their manufacture in accordance with the present invention, while illustrating appropriate alternatives. These examples are not intended to be limiting for the scope of invention outlined by the appended claims.

DETAILED DESCRIPTION OF THE INVENTION

As previously discussed there are several important requirements set on a material suitable for the inner container. It must be made of an autoclavable or radiation sterilizable polymeric material which is compatible with the stored products. The material must be possible to permanently weld to a bag and weld to other polymeric details, such as the mentioned saddle-formed port system, while also providing the possibility of forming rupturable peelable seal seams during modified welding conditions compared to the formation of permanent seams. Furthermore, the material should also be environment friendly and possible to recycle with a simple process. The material should be substantially impermeable for water vapor during steam sterilization, but need not be airtight according to the present invention, when an outer sealing envelope is used in combination with an oxygen scavenger. It would rather be an advantage if the material could permit an oxygen transfer so the oxygen scavenger can be able consume substantially all residual oxygen dissolved in the stored fluids. If radiation sterilization shall successfully be applied on the container in accordance with the International patent application PCT/SE95/00684, also the residual oxygen dissolved in the polymeric network of material of the inner container must be removed. The material must have a suitable aesthetic appearance and be clearly transparent and not tend to be discolored or opaque after sterilization. Finally, the material must maintain its flexibility and not become fragile or brittle after sterilization and storage.

A polymeric material for the inner container having all the mentioned characteristics is preferably is a flexible film having a region with a higher melt point designated as its outside and having a region with lower melt point designated as its sealing inside which can be sealed together by means of conventional welding tools to permanent or peelable seal seams. It is to be understood that the inner region is intended to face the stored agent or agents and can form both permanent seams and different peelable seal seams when subjected to different welding conditions or operations.

It is preferred that film is made of at least two different polymer layers of which at least the inner sealant layer is based on polyolefins, such as polyethylenes or polypropylenes of various qualities which are chemically inert to the stored fluids, autoclavable, weldable and possible to recycle. The terms "polyethylenes" and "polypropylenes" are intended to include both homopolymers and copolymers having such mentioned characteristics unless otherwise is specified. Preferably, the sealant layer is based on polypropylene including its copolymers with ethylene (propylene ethylene copolymer) and/or its mixtures with polyethylene.

However, since many conventional polyolefins, in particular polypropylenes, often have an insufficient flexibility and a certain brittleness, it is desirable to combine them with a polymer having an elastic property. In a specific embodiment according to the present invention it is therefore preferred to combine the polypropylene with a supplementary elastomer to improve its flexibility and resilience. The elastomer can be comprised in neighboring layer of the film or compounded with the polypropylene in the sealant layer. For multilayered materials it is preferred to have an inner, sealant layer comprising a high amount of polypropylene to benefit from its capacity of being inert towards the stored fluids and for facilitating the manufacturing of a container by means of different welding techniques. It is especially preferred that this layer can form both leaktight, but controllably rupturable, peelable seal seams at a predetermined temperature and permanent highly consistent seams when welding it together with different conditions, such as different welding temperatures or welding pressures. It is also desirable to introduce a flexible polymeric material with a high melting point that provides the material with an improved stability at the high temperatures locally reached during the welding. If such a material is comprised in a multilayered film, it should be placed as an outer, release layer and additionally be easy to print without migration of the printing ink. Suitable materials can be found among certain polyesters and copolymers thereof (copolyesters) and in particular cycloaliphatic polyesters.

A preferred material for the inner, primary container is made of a multilayered film comprising: a) an outer layer containing a copolyester, b) an inner sealant layer containing polypropylene, a propylene ethylene copolymer or a mixture of polypropylene or polyethylene and c) an interior layer containing a thermoplastic elastomer. In such a film the sealant layer further may comprise a thermoplastic elastomer which can be styrene-ethylene/butadiene-styrene block copolymer (SEBS) or suitable alternative elastomer having the appropriate mentioned characteristics. A material that has been proofed to be especially suitable for this type of inner containers is EXCEL brand of multilayered polymeric material from McGaw Inc., a multilayered polymeric material of about 200 micrometer thickness which is described in the European patent 0 228 819. EXCEL brand of multilayered polymeric material has a multilayered structure substantially comprising:

a) an inner, sealant layer facing the medical fluid consisting of a mixture of a polyethylene/polypropylene copolymer (FINA Dypro Z 9450) and KRATON G1652 brand of styrene/ethylene/butadiene/styrene copolymer from Shell (a styrene/ethylene/butadiene/styrene (SEBS) copolymer);

b) a middle, tie layer of pure EXCEL brand of multilayered polymeric material G652; and c) an outer, release layer of ECDEL 9965 (or 9566 or 9967) from Eastman Chemical Co. which is a cycloaliphatic thermoplastic copolyester (a copoly (ester ether), a condensation product of the trans isomer of 1,4-dimethyl-cyclohexanedicarboxylate, of cyclohexanedimethanol and hydroxyterminated polytetramethylene glycol).

The inner, sealant layer consists of a mixture of 80% copolymer of polyethylene and polypropylene with 20% of the elastomeric SEBS copolymer combined with minor additives of antioxidants and acid scavengers. The copolymer of polyethylene and polypropylene forms an interpenetrating network with the SEBS-copolymer which provides for a strong seal. This mixture seals itself over a broad range of temperatures and is capable of forming peelable seal seams of varying strengths, when welding in an interval of selected temperatures from about 85 to about 120° C. It has been demonstrated that welding at about 110 to 120° C. forms peelable seal seams which are easy to rupture by hand. It also provides for a suitable steam barrier and will, as shown below, in the exemplifying part, satisfyingly withstand both chemical and physical tests. The middle layer contains only the highly flexible copolymer KRATON G1652 brand of styrene/ethylene/butadiene/styrene copolymer with minor amounts of antioxidants. It contributes to the elasticity and the impact strength of the film. The outer layer of EXCEL brand of multilayered polymeric material is flexible and printable with a high melting point of 200° C. and contributes to an improvement of the welding capacity of the assembled film. When using EXCEL brand of multilayered polymeric material as the material for the inner bag formed container, it is preferred that the saddle formed port system which shall be attached to the sealant layer also contains polypropylene and preferably consists of a mixture of polypropylene and KRATON G1652 brand of styrene/ethylene/butadiene/styrene copolymer which is weldable to the inner layer of the EXCEL brand of multilayered polymeric material film. A suitable mixture is about 60% polypropylene and 40% KRATON G1652 brand of styrene/ethylene/butadiene/styrene copolymer. A preferred to use the saddle formed port system as disclosed in the Swedish patent application 9601540-9, also in the name of Pharmacia AB.

An inner container made of the preferred Excel® film has excellent characteristics for being autoclaved together with conventional parenteral nutrients. In addition, the EXCEL brand of multilayered polymeric material film is surprisingly compatible with lipophilic fluids. Even if its inner layer comprising a physical mixture of polypropylene and the SEBS polymer, tests involving its exposure to pure soybean oil (the main lipid constituent of the commercial lipid emulsion INTRALIPED lipid emulsion has not given any reasons to suspect the migration of potentially toxic agents. It will, however, have a relatively high oxygen permeability of about 1000 to 1600 cubic centimeters/$m^2$, atm, day, when measured at a specific temperature of 25° C. and 60% relative humidity and to comply with the requirements for long term storage of lipid emulsions and essential amino acid solutions it must be combined with an outer surrounding airtight envelope and an oxygen absorber. Even if inner containers made of EXCEL brand of multilayered polymeric material constitute suitable embodiments for the present invention also other polyolefin based films must be regarded as conceivable alternatives to use within the scope of the present invention, if they comply with the requirements mentioned above. It is therefore an important alternative to provide inner containers of a flexible, transparent film with a high degree of compatibility with lipophilic fluids from one or several layers consisting essentially only of or entirely of one or several polymers selected from a group consisting polypropylene, copolymers of propylene and ethylene, mixtures of polypropylene and polyethylene. For example, a layered film material comprising for example an inner sealant layer of propylene ethylene copolymer mixed with an elastomer, such as a SEBS polymer attached to an outer layer of pure polypropylene which is corona treated to be printable is a possible alternative material. Also a film consisting of an inner layer of ethylene containing polypropylene tied to a pure corona treated polypropylene layer by a polypropylene with a modified tacticity, such as REFLEX film from Rexene or Dow is a another conceivable alternative, as well as combinations of pure polypropylene layers having an improved elasticity and printability due to modifications in their molecular configurations or due to physical processing. For example, with metallocene type catalysts, a higher level of control of the stereoregularity of polypropylene chains can be obtained, as disclosed in Macromolecules, Vol. 28, 1995, pages 3771–8: W. J. Gauthier et al. This can yield profound effects on the physical properties of the material and impart e.g. highly flexible or elastomeric polypropylenes which can be included as future alternatives to EXCEL brand of multi-layered polymeric material. All such polypropylene based materials should be regarded as alternative embodiments of materials selected for the inner container, if they comply with the requirements set above.

As discussed in relation to the selection of material for the inner container, the material of the surrounding envelope must meet a number of demands to replace glass bottles. It must most importantly provide a high barrier against atmospheric oxygen. admitting an oxygen inflow preferably less than about 30 cubic centimeters/m$^2$, atm, day, when measured at a specific temperature of 25° C. and 60% relative humidity and more preferably less than 15 cc/m$^2$, atm, day and most preferably less than 5 cc/m$^2$, atm, day, when measured at the same conditions. It must be steam sterilizable at 121° C. for at least 30 minutes, while also having the capacity to withstand sterilization by irradiation to improve on existing aseptic overwrapping techniques. A conventional aluminum foil would meet such requirements, but will have the drawback of not being transparent to enable a visual inspection of the integrity of the stored material and for example an oxygen indicator. Furthermore, the envelope material must be strong and flexible, have a low impact on the environment and only contain such additives with the lowest possible tendency to spoil or interfere with the stored material by migration. The criterion of forming a barrier against oxygen can also be met by polyvinylidene chloride (PVDC), but it will, however, not be possible to steam sterilize and will not meet the demands of being environment friendly. As earlier discussed in the International patent application WO 94/19186, it was attempted to construct a multilayer film for packaging and autoclaving parenteral agents. This film was intended to support the oxygen barrier capacity of a poly(ethylene)-vinyl alcohol layer (EVOH) by introducing a water resistant and moisture absorbing outer structure to protect the EVOH-layer during the steam sterilization. Unfortunately, not even this multilayered film was capable to keep a satisfactory long time barrier against oxygen after its autoclavation. It was therefore highly desirable to improve such a film by adding to the EVOH-layer a protecting structure which not only was steam impermeable, but also could contribute to the oxygen barrier.

According to the present invention, it has been surprisingly found that if a first outer substantially water impermeable polymeric film with oxygen barrier forming capacity is assembled with a second, inner polymeric film with a comparatively higher oxygen barrier forming capacity at 25° C. at 60% relative humidity, a multilayered material suitable for forming an outer sealing envelope for the inventive container is obtained which can maintain such a high oxygen barrier as less than 5 ml oxygen per m$^2$, atm and day at a normal relative humidity, even after autoclavation and yet comply with the requirements set above.

Preferably, the outer film comprises a metal oxide coated polymeric layer connected to a second, inner film comprising an oxygen barrier forming polymeric layer. It is preferred that the outer film comprises a metal oxide, such as an oxide of silicon and/or aluminum and/or titanium together with at least one polymeric material, while the inner film preferably comprises an EVOH layer. Preferably, the outer film comprises a layer of polyethylene terephtalate coated with the metal oxide, while the inner film comprises at least one layer containing polypropylene. The outer film may comprise a second layer of polyethylene terephtalate (PET). In such cases, a first outer layer of polyethylene terephtalate (PET) is coated on one side with a metal oxide which is bound to a second layer of polyethylene terephtalate (PET). According to a specific alternative, both sides of a PET-layer is coated with metal oxide. The outer film can suitably contain a polyethylene terephtalate (PET) layer coated with a metal oxide of about 10–30 μm, preferably about 25 μm, thickness tied together to the inner film of about 50–200 μm, preferably about 100 μm thickness which preferably contains an EVOH layer tied together to surrounding polypropylene based (PP) layers (made of polypropylene, various copolymers of propylep and ethylene or mixtures thereof) in a conventional manner to obtain a multilayered material of the principal structure PET-metal oxide/glue/PP/tielayer/ EVOH/ tielayer/PP. This material will provide the oxygen barrier forming EVOH layer with an effectively protecting shield against moisture penetrating the polypropylene during steam sterilization and storage which otherwise will impair its subsequent barrier forming capacity. At the same time, the glassy, outer film will contribute to the oxygen barrier. The inorganic glassy metal oxide material consists of a thin metal oxide layer having a thickness of about 200 to 1200 Å and is deposited on a smooth polymer surface by a conventional technology, for example described in the European patent specification EP 0460796 (E.I. Du Pont De Nemours & Co.), wherein suitable PET-glass films are disclosed. The metal oxide may also be deposited on both sides of the film or a further PET layer can be added, so films of the structure glass-PET-glass-glue/PP/EVOH/PP or PET-glass/glue/PET/PP/EVOH/PP are obtained.

The glue binding the two films together is of a type conventionally used in adhesive bonding of multilayered polymer structures with a suitably low tendency to migrate. An especially suitable film is composed of PET-aluminum oxide/glue/PET/glue /PP/tie/EVOHI/tie/PP. In the following exemplifying part, it is demonstrated that it has excellent properties for constituting a protecting outer envelope in container for safely storing parenteral nutrients.

The oxygen absorber according to the present invention preferably is iron containing and dependent on water for its oxygen consumption, as described in the International patent application PCT/SE95/00684 in the name of Pharmacia AB. It is preferable that the ferrous oxygen absorber also can consume a certain amount of hydrogen sulfide degraded from sulfur containing amino acids, such as cystein in a stored solution comprising essential amino acids, as is disclosed in the German patent DE 42 33 817. The oxygen absorber shall be capable to withstand a sterilization procedure selected from steam sterilization and sterilization by means of irradiation without being impaired. The oxygen absorber can either be present in the container as a sachet or it can be compounded as a part of a multilayered film. It is preferred to use an oxygen absorber having a ferrous oxygen scavenging composition enclosed in one or several sachets or tray-like carriers placed close to the saddle-formed port system of the inner, filled container during the enclosure with a surrounding airtight envelope in a controlled atmosphere. For the preferred type of oxygen absorber, it is therefore important that there is a source of water present, either in the oxygen scavenging composition or elsewhere in the space wherein it shall exert its activity. Certain oxygen absorbers demand an atmosphere of at least 80% relative humidity (at 25° C.) for a maximum activity and would therefore require a high humidity in the closed space between the inner container and the envelope to ensure a correct function which typically is above according 60% in containers according to the present invention. This type of moisture dependent oxygen absorbers are preferred according to the present invention. The skilled person will have no difficulties in obtaining suitable oxygen absorbers in an appropriate amount when designing a container according to the present invention. An estimation of a necessary quality and amount can easily be performed from its oxygen predetermined consuming capacity when given values of the container, for example, of the volume of the stored material and the oxygen barrier capacity of the surrounding envelope. For example, if the total capacity of the oxygen absorber is at least 100 ml pure oxygen, this value must be higher than the amount expected to penetrate the envelope through a given area during a given time if the envelope is made of a material having an oxygen permeability of not exceeding 5 ml oxygen per $m^2$, atm and day at a normal relative humidity. An example of a suitable oxygen absorber, according to the present invention, is AGELESS FX200PA ferrous oxygen absorber available from Mitsubishi.

Figure 1:
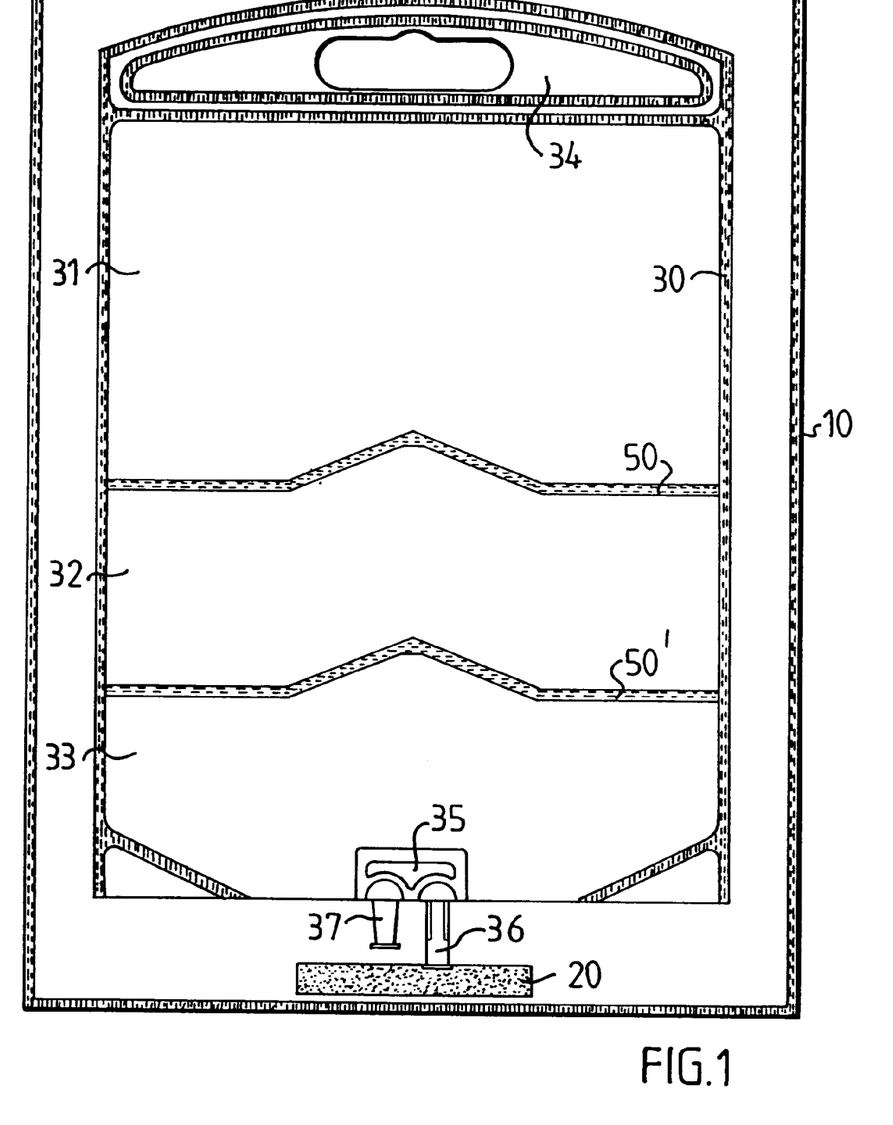
FIG. 1 schematically shows a plan view of a container according to a specific embodiment of the present invention.

In the specific embodiment illustrated in FIG. 1, the container has an outer sealing envelope 10 and an inner three-chamber container 30 filled with three different parenteral fluids. In the space between the envelope and the inner container, an oxygen absorber 20 is placed. In this space, also an oxygen indicator showing inadvertently penetrated oxygen from leakages, an indicator demonstrating a correct sterilization and other conditions optionally can be placed. Such indicators must, of course, be able to withstand the sterilization step, either with steam or radiation and they must not cause migration of toxic or potentially hazardous substances to the stored products.

The inner container shown in FIG. 1 is bag formed and provided with three parallel chambers 31, 32, 33 which may have the same or different volumes dependent on the desired amount of the stored product. The inner container is illustrated as being provided with a handle part 34 in its top to facilitate conventional administration from a hanging position. The bottom of the container is provided with a port system 35 which can be a conventionally formed saddle port welded to the container material during the manufacture. A preferred port system which is designed to be more easily sterilized is described in a parallel, as yet unpublished, Swedish patent application.

The port system has an outlet port 36, through which fluid communication to a patient in need of fluid therapy can be established by conventional infusion devices which, however, not are discussed in more detail. Through an inlet port 37 of the port system, it is possible to introduce an additional agent to the fluids of the container in any desired moment. Such agents are typically supplementary drugs or nutrients or micronutrients which can not be stored together with fluids of the container.

In this embodiment, the three chambers 31, 32 and 33 are filled with three different parenterally administerable nutrients in fluid forms which, just before their administration to the patient, shall be homogeneously mixed together to form a total parenteral nutrition (TPN) solution. To enable such mixing at will, the chambers are divided by such seams that can readily be ruptured by the user from the outside of the container. The two seams 50,50' separating the chambers are typically formed by peelable seal weldings in the container which are highly leak tight, but possible rupture by a predetermined motion of the user. Peelable seals or weak weldings belong to a well-known technique in the art processing of polymers and the conditions about their formation and characteristics are described more in detail in U.S. Pat. No. 5,128,414 or in the European patent specifications EP 0 444 900 and EP 0 345 774 which documents hereby are incorporated as references. A particularly preferable construction of the welded peelable seal seams, suitable for a container according to the present invention, will be discussed in greater detail below.

In the specific embodiment of a container according to FIG. 1, one chamber contains a carbohydrate solution comprising glucose, one chamber contains a lipid emulsion typically comprising 10–30% (w/w) of a lipid, such as INTRALIPID lipid emulsion of Pharmacia AB, and one chamber contains an amino acid solution such as VAMIN amino acid solution from Pharmacia AB, if suitable comprising the essential amino acids. Such parenterally administerable nutrients and their appropriate additives for giving total parenteral nutrition and/or complementary drug therapy are described in more detail in other documentation, such as the European patent application 0 510 687 in the name of Green Cross Corp. which is incorporated as a reference in its entirety. When suitable for clinical reasons, each of these three nutrients can comprise further constituents, such as trace elements, electrolytes, vitamins, energy substrates, supplementary therapeutic agents and agents supporting the metabolization of said nutrients. However, it must be carefully analyzed for each constituent, in which chamber it shall be stored with maintained integrity and minimal interference with the selected nutrient.

The designation of the chambers 31,32,33 for the three mentioned nutrients has been done after careful consideration of both convenience and safety aspects. For such a reason, it is preferred that either the amino acid solution or the lipid emulsion is contained in the bottom chamber 33, since, if the user, for some reason, would be unsuccessful in correctly performing the mixing procedure, the infusion of a pure amino acid solution or a lipid emulsion leaves the patient unaffected compared to an accidental infusion of pure glucose solution which could lead to unwanted side effects, for instance, if the patient suffers from complications related to diabetes. It is therefore preferred that the top chamber 31 is filled with the carbohydrate solution which also is of advantage when considering its relatively larger volume can be used to exert a sufficient pressure to rupture the upper peelable seal 50 when mixing the nutrients.

According to one embodiment, the middle chamber 32 contains the lipid emulsion, so it may serve as a visual or optical leak detector if any leakages in the seals between chambers will appear during the storage, while the lower chamber 33, facing the port system is designated for the amino acid solution. As an alternative embodiment, the lower chamber 33 may contain the lipid emulsion having the smallest volume. This is will give the filled chambers a similarly shaped volume extension and heat penetration during the steam sterilization in order to obtain a similar temperature gradient in all the three chambers.

However, in certain applications the convenience of opening the chambers for fluid transfer by rupturing a peelable seal are given priority. For example, it might be desired to have the constituent with the largest fluid volume designated for the top chamber in order to use its mass for rupturing the peelable seal seams, regardless of the contents of the chambers. It should also be understood that other chamber configurations than the three parallel chambers shown in FIG. 1 is conceivable within the scope of invention.

Besides parenteral nutrients it is conceivable to store a large number of other parenterally administerable products in a container according to the present invention, also such that are in solid powdered or lyophilized forms can be stored together with diluents and other parenteral fluids when appropriate for stability reasons.

A container according to the present invention is preferably manufactured with an inventive method wherein a flexible polymeric multilayered material is introduced in bag forming station where a bag shaped sealed inner container is manufactured by welding together polypropylene containing sealing layers of the material and where optionally at least two chambers are formed by welding at least one partitioning peelable seal seam at a lower temperature. During the bag forming process a side of said inner container is provided with at least one temporary opening, whereupon the inner container is filled with at least one parenterally administerable fluid through said temporary opening. The temporary opening at the side of said inner container can then be sealed by welding permanent seams and the filled and sealed inner container is enclosed in an oxygen barrier forming envelope together with an oxygen absorber and the so final sealed container is sterilized.

Preferably, the polymeric material for the inner container is in the form of thin flexible sheet in a suitable, predetermined size when introduced to the bag forming process. The sheet is first attached to a sealed port system for fluid communication, preferably of the saddle-formed type described above, whereupon the port system is welded to the sheet. When attaching the port system the sheet may first be penetrated by a suitable tool, so to form one or several orifices in the sheet corresponding to the number of orifices of the port system. Preferably, two such orifices are made to correspond with an exit and an inlet port.

A bag shaped sealed inner container with two identical faces, a bottom, a top and two sides is formed around the bottom with the attached port system in its bottom by welding together the polypropylene containing sealing layers of the material by conventional welding tools, thus forming two side seams and a top seam.

Although the above described forming of the bag is preferred according to the present invention, it would in certain applications be conceivable and regarded as a part of the present invention, to, as an alternative, start the manufacture from a blown tubular parison of polymeric material and by welding form permanent sealing seams in its top and bottom and provide for the attachment of a port system in its bottom seams. Filling ports for the chambers must thereby be attached during said welding procedure. This type of manufacturing process suitable for preparation of inner containers having one or two chambers, but less suitable if three or more chambers are preferred. The manufacturing process may as another alternative start from two sheets which are welded together with four seams around to form a bag shaped inner container having a sealed port system for fluid communication welded in its bottom seam. Such an inner container can be provided with peelable seal seams between its storage chambers and alternative temporary filling ports, as disclosed below.

If two or more chambers are desired for separate storage of two or more agents, at least one leak tight peelable seal seam is formed as partitions between the chambers of the inner container which are possible to rupture by hand in a predetermined manner. By welding at a specific, lower temperature compared to the previously mentioned permanent weldings such peelable seals can be manufactured. As will be discussed below in greater detail the peelable seal seams can be made with a specifically designed zone to obtain an initial rupturing point to facilitate their manual opening when it is desired to mix the stored contents within the container.

To enable filling of the inner container it is provided with at least one temporary filling port in the side of the bag shaped inner container which subsequently to completed filling is sealed with a permanently welded seam. The filling is preferably performed in a controlled atmosphere and in connection with a blast of an inert gas, such as nitrogen or helium, to remove air from the inner container.

According to a first embodiment of the manufacturing method, one or several specific provisional filling tubings designated for one or several fluid agents are attached in the seam of the inner container during the welding. The chambers can then be filled with one several parenterally administerable fluids by through the provisional filling tubings by sealing connection to filling nozzles of a conventional filling equipment. After the filling is completed, the side provided with filling tubings attached to the seam is cut off, whereupon the side is re-sealed with a permanently welded seal.

According to a second embodiment of the manufacturing method, one side of multi-chamber inner container is sealed by means of a weak welding which can be ruptured by means of the filling equipment in order to form at least one temporary opening in the side seam. Preferably, the weak side seam is welded so as two sleeves are formed from the edges of the sheet outside the weak seam to enable the filling equipment to open the seam by a peeling. For example the filling equipment can be provided with one or several twistable rods which opens the seam by a peeling motion in connection with that one or several filling nozzles are introduced in the inner container from its side, preferably in a controlled atmosphere in connection with a blast of an inert gas, as mentioned above. After the filling is completed the filling nozzles are removed and the side of the inner container is re-sealed with a permanent welding seal. It is to be understood that alternative means for open the peelable seal to form temporary opening for filling can be employed. for example the filling nozzles may provided peeling means in the form of protruding devices which may perform a twisting, peeling motion. After filling and removing the nozzles, the side of inner container is welded and sealed by a permanent seam.

According to a third embodiment at least one filling orifice is formed in a side seam of the container with a shape corresponding to a filling nozzle of the filling equipment in order to provide a sealing connection between the orifice and the nozzle during the filling procedure. Such filling orifices can be formed by directly shaping the flexible material to an orifice having a form corresponding to the nozzles or by attaching a separate orifice to the side of the inner container when forming a side seam.

The level of filling or amount of head space in each chamber must be carefully controlled. It is desired that the filling level of each chamber is, if not identical, at least comparable which is advantageous for obtaining the same heat penetration of the filled products during the heat sterilization. When desiring the level of filling it must be considered that a large head space volume from a low filling level might lead to that a sensitive lipid emulsion partially breaks up if the container is unintentionally shaken during its handling. A small head space volume from a high filling level will lead to difficulties in reading a correct fluid level in the container.

The completely assembled and filled inner container is enclosed in an oxygen barrier forming envelope together with an oxygen absorber and optionally together with one or several visual indicators. The finally assembled container can now be sealed by permanently welding the envelope together in tool operating in a controlled, if desired, inert atmosphere. The container can now be sterilized by means of steam at about 120° C. (autoclavation) or by sterilizing gamma radiation. The described inventive manufacturing method is advantageous for industrial production of parenteral nutrients and minimizes the utility of a controlled atmosphere and the use of inert gases is reduced to one step where the inner container is filled which is highly resource saving and guarantees a simplified production process. Furthermore, the filling employs provisional, openings at the side of the container which minimizes the risk for leakages conventionally experienced in connection with permanently attached filling ports. Such a filling also gives the benefits of a smaller enclosing envelope and a shorter autoclave program.

The previously described peelable seal seams, serving as leak tight partitions between the chambers during storage in the inner container, must be easy to open manually by the user in a simple predetermined manner from the outside of the container, preferably without removing its enclosing envelope. According to the present invention, the peelable seal seams are preferably straight seams provided with a rupture zone.

Figure 2A:
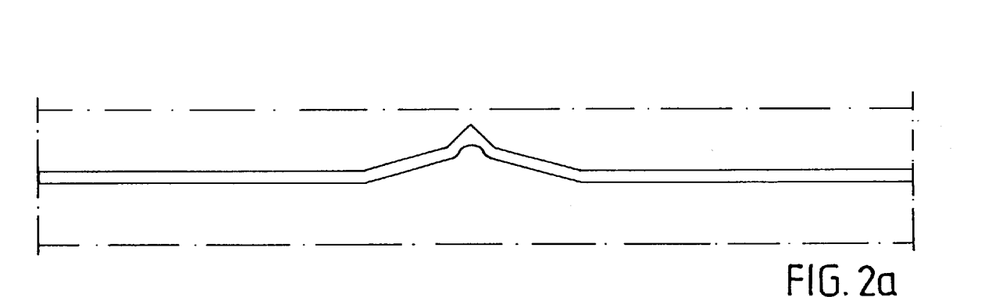
FIG. 2a and FIG. 2b schematically show two examples of peelable seal seams according to the present invention.
Figure 2B:
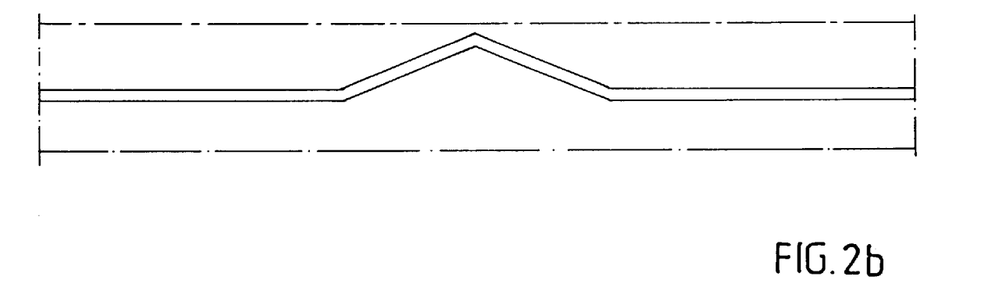

According to the embodiments demonstrated in FIG. 2a and FIG. 2b, the rupture zone of such a peelable seal seam comprises a point where two straight seams meet in angle. A small or sharp angle will be easy to rupture by the user, but it will at the same time create a risk for unintentional opening when handling the container. Such a seam will enable a surprisingly easy rupturing or peeling process by providing a concentration of the opening forces on a single point in the angle of the seam, whereupon it can be easily peeled apart. In contrast, a very large angle will provide a seam that is difficult to open. It is desired to obtain a optimized angle which gives initial opening resistance of the seam while providing a successively reduced resistance as the opening proceed towards the sides of the container, when the fluid enters between the foils and separates them. When having a sufficiently large angle, the opening force and the foils will become almost perpendicular to the seam which facilitates the opening process. A too small angle might also lead to the appearance of hole in the middle of the seam, but no further opening of the seam, since the lines of forces on the opening point will have tangential direction and not contribute to the opening of the remaining seam. For embodiments of FIG. 2a and 2b and similarly formed seams, the angle of the seam (or in the projection of the seams when having curves in the seam) is at least 90°. Preferably, the angle is less than about 170° and more preferably between about 110° to 160°. According to specifically preferred embodiments, the angle is between about 120° to 140° and according to two experimentally well functioning embodiments about 120° or about 140°. Both rupture zones demonstrated in FIG. 2a and 2b will provide for local reductions in the opening force which considerably facilitates a manual opening of the peelable seals. As also demonstrated in FIG. 2a the rupture zone can comprise a curved part of the seam. It may also be advantageous to round one or several sharp sections of the seam in order to control the manual forces required for the rupture process. The seams according to FIG. 2 have will provide easy peelable openings in a container having a length of 450 mm including a handle part and a width of 300 mm, as illustrated in FIG. 1. Such seams can readily be opened by different handling techniques which are intended to be a part of the instructions of the container. The seams are suitably opened while still having the outer enclosing envelope protecting the inner container which gives the benefit of prolonged protection.

The rupture zones preferably are positioned in the middle of the seam, so it can be successively opened from the middle towards the sides, since this may enable a highly reproducible opening procedure by the user from the outside of the bag. The rupture zone typically has an extension of less than half the entire seam, preferably less or equal than about 40% of the seam and more preferably less than about one third of the seam length. The width of the weak seal seams are typically less than 10 mm and preferably about 3 to 8 mm and exemplified as about 6 mm in the seams demonstrated in FIG. 2a and 2b. Alternative designs of the rupture zone to what have been exemplified in FIG. 2a and 2b and discussed above are conceivable to the skilled person if they can comply with the demands of being leak tight during storage and transportation and yet are readily opened manually according to simple instructions. For example, the peelable seal seam can be made entirely straight and by various means such as variations in the welding pressure and/or temperature and differently shaped welding tools.

Suitable peelable seal welding temperatures for the above mentioned EXCEL brand of multilayered polymeric material material in the inner container are in the range of 106–121° C. using a pressure of about 315±20 N of the welding tool for 2–10 second with gauge meter of about 0.3 mm. Such seams are demonstrated to be suitably leak tight after being subjected to conventional mechanical package tests and are objectively easy to open, also after the container has been subjected to steam sterilization at 121° C. for about 20 minutes.

A first preferred opening procedure is to gently roll up the container from the upper side (the side opposite to the attached port system) and thereby make use of the volume of the largest chamber, suitably containing a glucose solution, to exert a pressure large enough to rupture the seal in its weakest point and peel apart the seam towards the sides of the container. Another preferred way of opening the seal is to pull the front and the rear walls of the inner container apart from one another by a careful pulling motion so a rupture is formed in the weakest spot of the seal which thereby may be easy to peel apart.

When making an inventive container ready for use, its peelable seal seams can be ruptured in a predetermined manner as discussed above. The stored parenteral agents can thereby be mixed in a mixing chamber constituting the entire volume of the inner container. If necessary the container can be gently agitated to a homogenous fluid suitable for immediate administration. For the alternative of mixing a separately stored lipid emulsion, an amino acid solution and carbohydrate solution, it can be readily mixed into a TPN-solution in a highly convenient manner. The enclosing envelope can be removed and if desired supplementary agents can be introduced through the port system to be admixed to container. The inner container is now completely ready to be used and, if desired hanged on a rack by means of the hanger or other ready made means of the container before connecting to a patient, for example by using a conventional infusion device after penetrating the outlet port of the port system. The inventive container is aimed to be adapted to a large number of conventional infusions sets and such details will not be discussed here in further detail, since they are not a part of the present invention.

EXAMPLE 1

This example shows the stability of INTRALIPID lipid emulsion 20% in a 500 ml EXCEL brand of multilayered polymeric material polymer inner container wrapped in an enclosing envelope made of the layers PET-aluminum oxide/glue/PP/EVOH/PP given the trade name Oxnil (Pharmacia & Upjohn AB), together with an oxygen absorber (AGELESS FX200PA ferrous oxygen absorber FX100 from Mitsubishi Gas Co.) INTRALIPID lipid emulsion 20% in a 500 ml glass bottle is used as a reference.

INTRALIPID lipid emulsion 20% stored in a container according to the present invention was compared with INTRALIPID lipid emulsion 20% stored in a glass bottle at 25° C. and 60% relative humidity for 18 months. After 18 months storage the pH values and the amounts of free fatty acids (FFA) and lysophosphatidyl choline (LPC) were tested. The mean droplet size was measured according to conventional routines employed by manufacturers of intravenous lipid emulsions in the pharmaceutical industry.

|  | Months storage | Peroxides (mEq/l) | pH | LPC (mg/ml) | FFA (mmol/L) | Mean droplet size (nm) |
|---|---|---|---|---|---|---|
| Emulsion stored in glass | 12 | 0.0 | 7.2 | 0.69 | 2.3 | 387 |
|  | 18 | 0.1 | 7.1 | 0.84 | 2.7 | 348 |
| Emulsion stored in polymer container | 12 | 0.0 | 7.5 | 0.74 | 2.2 | 334 |
|  | 18 | 0.0 | 7.3 | 0.83 | 2.7 | 335 |

(Mean values of five batches)

The initial pH-values were about 8.0–8.4 and decreased after storage, as would be expected due to an increase in free fatty acids (FFA) and lysophosphatidyl choline from hydrolysis of triglycerides and phospholipids. A minor weight loss was measured on the polymer containers about 0.6% after 12 months and about 0.8% after 18 months.

This test demonstrates that the container according to the present invention exhibits an entirely comparable storage capacity in relation to glass containers in protection against degradation and physical changes that deteriorates the emulsion quality. Emulsions stored in the inventive container will consequently have a shelf life of at least 18 months when stored during normal conditions.

EXAMPLE 2

The oxygen barrier forming capacity of the material selected as an envelope for the inner filled container is tested.

The envelope material consists of a multilayered polymer structure of PET-metal oxide/glue/PP/EVOH/PP as disclosed, above in Example 1.

In order to determine the benefit of the PET-metal oxide layer, such a film (Film 1) is compared to a conventional PP/EVOH/PP (PP=polypropylene and EVOH=((poly)-ethylene vinyl alcohol) film (Film 2) for oxygen permeability measured in ml oxygen penetrated per day and m², at two different temperatures and at 75% relative humidity. The permeability tests were performed with standard Mocon permeability measurements.

|  | Film 1 (ml/day, m²) | Film 2 (ml/day, m²) |
|---|---|---|
| 25° C. | 1.1 | 4 |
| 40° C. | 2.9 | 23 |

It is obvious that the PET-metal oxide containing film (Film 1) complies with the requirements of having an oxygen permeability of less than 5 ml/day, m² The PET-metal oxide film was also subjected to chemical and mechanical tests after being steam sterilized according to the European Pharmacopoeia and exaggerated test at 121° C. for 60 minutes. It was found the material also fulfills the demand of the European Pharmacopoeia when considering the migration of components from the film, as well as having excellent values in terms of absorbance, alkalinity/acidity, oxidizable substances and appearance of the stored solution.

EXAMPLE 3

This example aims to study the mixing properties into a safely administerable TPN-solution of one batch of lipid emulsion stored in a container according to the present invention for 12 months at +5° C. and +25° C.

INTRALIPID lipid emulsion 20% filled in 500 ml inner containers made of EXCEL brand of multilayered polymeric material were stored with an oxygen absorber in an enclosing envelope made of the layers PET-metal oxide/glue/PP/EVOH/PP, as disclosed in Examples 1 and 2.

The so stored lipid emulsion was brought together with a 1000 ml amino acid solution (VAMIN amino acid solution 14 g N/l) and 1000 ml glucose solution (Glucose 20%). 10 ml ADDIPHOS phosphate solution were added to the glucose solution. SOLUVIT vitamin preparation reconstituted in VITALIPID lipid preparation was added to the lipid emulsion and conventional electrolytes (ADDAMEL electrolyte, ADDEX electrolyte NaCl, Addex® KCI and CaCl₂ 1M) to the amino acid solution. After gentle agitation, the mixture was transferred to a 3 liter IV bag with its air expelled which was agitated thoroughly to ensure proper mixing. Part of the bag was dispensed into a glass bottle for analyze day 0 and day 6.

The IV bag with its remaining content was stored flat horizontally for 6 days at cold temperature about +5° C. followed by one day in room temperature about +25° C. when it was hung vertically. The glass bottles were stored at room temperature for 7 days and 24 hours, respectively. To be considered physically stable the admixtures must pass the inspection after 24 hours storage at room temperature and 6 days storage at cold temperature followed by one day at room temperature.

| Mean droplet size ($\mu$m) (D(4, 3), Malvern mastersizer | 0 days | 6 + 1 days |
|---|---|---|
| +5° C. | 0.37 | 0.39 |
| +20° C. | 0.37 | 0.38 |

The appearance of the emulsions was approved according to a conventional visual inspection performed as a standard routine by experienced emulsion manufacturers. A cream layer varying between 1 and 3.5 mm was present in all admixtures. It was, however easily redispersed by gentle agitation. There were no significant change in mean droplet size or drop size distribution after 6+1 days storage. The fraction of droplets less than 5.29 $\mu$m were 100% in all samples when measured with a Malvern Mastersizer and there were no droplets larger than 8 $\mu$m in any of the samples according to an investigation with a phase contrast microscope.

The admixtures tested were satisfactory physically stable according emulsion appearance.

EXAMPLE 4

The mixing properties of INTRALIPID lipid emulsion 20% (20% soybean oil fat emulsion from Pharmacia AB), filled and steam sterilized in three chamber inner containers made of EXCEL brand of multilayered polymeric material , was compared to INTRALIPID lipid emulsion 20% heat sterilized and stored in a glass bottle. Each three chamber container was purged with filtrated nitrogen two times immediately prior to the filling and 500 ml nonsterile INTRALIPID lipid emulsion was transferred into the middle compartment from glass bottles. The other compartments were filled 614 and 1193 ml water for injection, respectively. The filled and sealed container was placed in an envelope made of PET-metal oxide/glue/PP/EVOH/PP, as mentioned in earlier examples, with an oxygen absorber between the outlet and the inlet port of the saddle formed port system. Before sealing the envelope, it was evacuated in a Multivac before nitrogen was flushed into the envelope to a suitable gas volume for sterilization, whereupon it was sealed. The container was thereafter autoclaved corresponding to 17 to 20 minutes at 121.1° C. The reference glass bottle was autoclaved corresponding to 12 minutes at 121.1° C., according to a regular manufacturing process. The mixing was carried out under aseptic conditions in the same order is if mixing was performed in a three chamber container. A 17.2% glucose solution was transferred to the mixing vessel under nitrogen protection, whereupon lipid emulsions (INTRALIPID lipid emulsion 20%) treated as above, was added and after gentle shaking amino acid solution (VAMIN amino acid solution 18 with electrolytes) was admixed and agitated. The admixtures were dispensed into sterile infusion bottles under nitrogen protection. After sealing the bottles, they were stored at ambient temperature (about 25° C.) for two days or at about 5° C. for 6 days followed by 2 days at about 25° C.

The admixtures were tested for creaming (visual inspection of the cream layer), emulsion appearance (visual inspections of oil droplets on surface and glass walls) and mean droplet size and droplet size distribution (Malvern Mastersizer)

No obvious difference could be found in creaming or emulsion appearance between the different admixtures.

The following mean droplet sizes in $\mu$m were found for admixtures with lipid emulsion from glass bottle and mean values from three different batches stored in the polymer container, respectively,

| Storage time/temp. | glass bottle | polymer container |
| --- | --- | --- |
| 48 h at about 25° C. | 0.40 | 0.43 |
| 6 days at 5° C. and 48 h at 25° C. | 0.42 | 0.44 |

The results show that lipid emulsion autoclaved in three chamber polymer containers maintain their mixing properties and do not physically deteriorate, when compared to emulsions autoclaved in glass bottles.

By its high integrity of the stored constituents, its specific chamber configuration in multi-chamber embodiment and facilitated mixing provisions, the container considerably improves both the safety and the convenience for the patients dependent on long-term administration regimens when compared both to conventional mixing systems consisting of individual glass bottles and comparable flexible container with a shorter shelf life. Even the most oxygen sensitive amino acids will now be possible to comprise in during long term storage by using the inventive containers. The inventive containers are also highly suitable for being industrially manufactured in a large scale by a forming, filling and sealing procedure of the inner containers which subsequently are assembled to the final container and sealed in an outer envelope, with a minimum of requirements of an oxygen deprived atmosphere, before finally being sterilized and stored.

We claim:

1. A flexible transparent container for improved storage of oxygen sensitive parenterally administrable agents comprising an inner, primary container enclosed in a substantially oxygen impermeable outer envelope with an oxygen absorber, capable of consuming essentially all residual oxygen after the outer envelope is sealed as well as the oxygen penetrating said envelope characterized in that:

(i) the inner container is made of a polypropylene containing flexible polymeric material compatible with lipophilic agents capable of forming both permanent and peelable seals, the inner container made of a multilayered film comprising;
      a) an outer layer containing a copolyester,
      b) an inner sealant layer containing polypropylene, a propylene ethylene copolymer or a mixture of polypropylene or polyethylene and
      c) an interior layer containing a thermoplastic elastomer;
   (ii) the envelope is made of a substantially water impermeable flexible multilayered polymeric material comprising:
      a) a first outer substantially water impermeable polymeric film with oxygen barrier forming capacity, assembled with
      b) a second, inner polymeric film with a supplementary oxygen barrier forming capacity;

and in that the container essentially maintains its characteristics after being subjected to sterilization by steam or radiation.

2. A container according to claim 1 characterized in that the inner, primary container is divided into two or more chambers by one or more leak tight peelable seals, possible to rupture by hand from the outside when the contents of the chambers are desired to be mixed and administered to a patient.

3. A container according to claim 2 characterized in that container has at least three chambers comprising an upper chamber, at least one middle chamber and a lower chamber provided with a port system for dispensing a mixed fluid product made from its stored agents and for introducing a supplementary agent.

4. A container according to claim 3 characterized in that said upper chamber is designated to be filled with the agent having the largest volume.

5. A container according to claim 4 characterized in that the inner container has three chambers each designated for a fluid parenteral nutrient of which the lower chamber contains either a lipid emulsion or an amino acid solution.

6. A container according to claim 5 characterized in that the carbohydrate solution comprises glucose and the amino acid solution comprises the essential amino acids.

7. A container according to claim 3 characterized in that the inner container has three parallel chambers of which the upper chamber is filled with a carbohydrate containing aqueous solution, the middle chamber with a lipid emulsion and the lower chamber with an amino acid containing aqueous solution.

8. A container according to claim 3 characterized in that the inner container has three parallel chambers of which the upper container is filled with a carbohydrate containing aqueous solution, the middle chamber with an amino acid containing aqueous solution and the lower chamber with a lipid emulsion.

9. A container according to claim 2 characterized in that the peelable seals seams dividing the chambers of are provided with a rupture zone with reduced strength.

10. A container according to claim 9 characterized in that the rupture zone comprises a point where two straight seams meet in an angle.

11. A container according to claim 10 characterized in that the angle is at least 90°.

12. A container according to claim 9 characterized in that the rupture zone comprises at least one curved part of the seam.

13. A container according to claim 9 characterized in that the weak seam is straight in the rupture zone.

14. A container according to claim 9 characterized in that it comprises at least two parallel peelable seal seams.

15. A container according to claim 9 characterized in that said rupturable zone is welded with less pressure and/or temperature.

16. A container according to claim 1 characterized in that the inner, primary container is made of a flexible film having a region with higher melt point designated as its outside and a region with lower melt point designated as its sealing inside.

17. A container according to claim 16 characterized in that said inner region with lower melt point is capable of forming both permanent seals and peelable seals when subjected to different welding conditions.

18. A container according to claim 1 characterized in that the outer layer can be subjected to a printing process without subsequent migration of printing ink.

19. A container according to claim 18 characterized in that the outer layer contains a polyester or a copolyester.

20. A container according to claim 1 characterized in that the sealant layer further comprises a thermoplastic elastomer.

21. A container according to claim 1 characterized in that the thermoplastic elastomer is a styrene-ethylene/butadiene-styrene block copolymer.

22. A container according to claim 1 characterized in that the sealing envelope is made of a flexible multilayered transparent material which, after steam sterilizing at 121° C., provides an oxygen barrier with an oxygen penetration less than 30 cubic centimeters/m$^2$, atm, day, when measured at a specific temperature of 25° C. and 60% relative humidity.

23. A container according to claim 22 characterized in that said envelope forming multilayered material consists of a first outer water impermeable film comprising a metal oxide coated polymeric layer connected to a second inner film comprising an oxygen barrier forming polymeric layer.

24. A container according to claim 23, wherein said outer and inner film is connected by adhesive bonding.

25. A container according to claim 23, wherein the oxygen barrier forming layer of said second inner film comprises (poly)-ethylene vinyl alcohol (EVOH).

26. A container according to claim 23 wherein said second inner film comprises at least one layer containing polypropylene.

27. A container according to claim 23, wherein the first outer film comprises a second layer of polyethylene terephtalate (PET) layer.

28. A container according to claim 27, wherein the first outer film has a first outer layer of polyethylene terephtalate (PET) layer having one side coated with a metal oxide bound to a second layer of polyethylene terephtalate (PET) layer.

29. A container according to claim 28, wherein the first outer polyethylene terephtalate (PET) layer is coated with metal oxide on both sides.

30. A container according to claim 22 characterized in that said outer film comprises a polyethylene terephtalate (PET) layer coated with a metal oxide.

31. A container according to claim 30 characterized in that the metal oxide is selected from silicon oxides, aluminum oxides and titanium oxides.

32. A flexible transparent container for improved storage of oxygen sensitive parenterally administrable agents comprising an inner, primary container enclosed in a substantially oxygen impermeable outer envelope with an oxygen absorber, capable of consuming essentially all residual oxygen after the outer envelope is sealed as well as the oxygen penetrating said envelope characterized in that:

(i) the inner container is made of a polypropylene containing flexible polymeric material compatible with lipophilic agents capable of forming both permanent and peelable seals;

(ii) the envelope is made of a substantially water impermeable flexible multilayered polymeric material comprising:
   a) a first outer substantially water impermeable polymeric film with oxygen barrier forming capacity, assembled with
   b) a second, inner polymeric film with a supplementary oxygen barrier forming capacity;

and in which the container essentially maintains its characteristics after being subjected to sterilization by steam or radiation, in which the sealing envelope is made of a flexible multilayered transparent material which, after steam sterilizing at 121° C., provides an oxygen barrier with an oxygen penetration less than 30 cubic centimeters/m$^2$, atm, day, when measured at a specific temperature of 25° C. and 60% relative humidity, wherein said envelope forming multilayered material consists of a first outer water impermeable film comprising a metal oxide coated polymeric layer connected to a second inner film comprising an oxygen barrier forming polymeric layer, wherein said second inner film comprises at least one layer containing polypropylene, and wherein said envelope forming material consists of a film having the structure PET/metal oxide/glue/PET adhesively bound to a film consisting of the structure polypropylene/tielayer/EVOH/tielayer/polypropylene.

* * * * *